(12) United States Patent
Zou et al.

(10) Patent No.: US 10,175,511 B2
(45) Date of Patent: Jan. 8, 2019

(54) MEASUREMENT TECHNIQUES FOR LIQUID CRYSTAL PARAMETERS INCLUDING TWIST ELASTIC CONSTANT WITH LIGHT MEASUREMENT

(71) Applicant: INSTEC, INC., Boulder, CO (US)

(72) Inventors: Henry Zhong Zou, Louisville, CO (US); Lianhua Ji, Erie, CO (US)

( * ) Notice: Subject to any disclaimer, the term of this patent is extended or adjusted under 35 U.S.C. 154(b) by 0 days.

(21) Appl. No.: 15/600,472

(22) Filed: May 19, 2017

(65) Prior Publication Data

US 2017/0255040 A1  Sep. 7, 2017

Related U.S. Application Data

(62) Division of application No. 14/820,626, filed on Aug. 7, 2015.

(51) Int. Cl.
| | |
|---|---|
| *G01R 31/26* | (2014.01) |
| *G02F 1/13* | (2006.01) |
| *G01N 11/00* | (2006.01) |
| *G02F 1/1343* | (2006.01) |
| *G02F 1/00* | (2006.01) |

(52) U.S. Cl.
CPC ........... *G02F 1/1309* (2013.01); *G01N 11/00* (2013.01); *G02F 1/0045* (2013.01); *G02F 1/134309* (2013.01); *G02F 1/134363* (2013.01)

(58) Field of Classification Search
CPC ... G01N 27/041; G02F 1/1309; G02F 1/1333; G02F 1/1391; G09G 3/39; G09G 3/2014; G09G 3/2077; G09G 3/3629; C09K 19/02; C09K 19/18; C09K 19/586; C09K 19/588; C09K 19/0275
See application file for complete search history.

(56) References Cited

U.S. PATENT DOCUMENTS

| | | | |
|---|---|---|---|
| 5,550,664 A * | 8/1996 | Tsuda | G02F 1/1391 349/124 |
| 7,389,677 B2 | 6/2008 | Uchida et al. | |
| 8,013,819 B2 * | 9/2011 | Ben-Shalom | G09G 3/3629 345/87 |
| 2004/0155222 A1 * | 8/2004 | Kagawa | G02F 1/134363 252/299.01 |
| 2009/0284262 A1 * | 11/2009 | Wand | G01N 27/041 324/453 |
| 2011/0007260 A1 * | 1/2011 | Chien | C09K 19/02 349/186 |

* cited by examiner

*Primary Examiner* — Minh N Tang
(74) *Attorney, Agent, or Firm* — Wilson Daniel Swayze, Jr.

(57) ABSTRACT

Provided is a set of techniques for measuring different properties or parameters of liquid crystal mixtures by applying a driving waveform and measuring the response current and/or the optical response. This may be done by using specific liquid crystal test cells. Also provided are the optimized test cell parameters that are used in the algorithms for calculating the properties.

11 Claims, 10 Drawing Sheets

Step 1. K22 test cell characterizing with reference NLC a. Select a set of test cells (> 3 )
        1. Rubbing direction 0~3º for positive LC and 87~90 º for negative LC
        2. Each test cell has different cell gap than any of others
        3. Same electrode pattern
    b. Fill the test cells with the same reference NLC
    c. Measuring the $V_{th}$s of all above test cells
    d. Derive the cell feature factor, $\alpha$, by fitting (equition 1.5) all above $V_{th}$s using their corresponding cell gap, $d$ as variable Step 2. Measuring unknown NLC K22 with characterized test cell a. Fill one of characterized test cell in the Step1
    b. Measuring $V_{th}$s of filled test cell
    c. Calculate K22 with Equations 1.3 and 1.4 by applying the cell feature factor, $\alpha$, from Step 1 and known cell gap $d$, here we assume $\varepsilon\Delta$ is a known parameter or already measured using Instec's ALCT

Fig. 6

MEASUREMENT TECHNIQUES FOR LIQUID CRYSTAL PARAMETERS INCLUDING TWIST ELASTIC CONSTANT WITH LIGHT MEASUREMENT

This application is a Divisional of U.S. patent application Ser. No. 14/820,626, filed Aug. 7, 2015, which is incorporated herein by reference in its entirety.

BACKGROUND

The disclosure herein relates generally to techniques and equipment that may be used in conjunction with measuring liquid crystal parameters and ion impurities.

Liquid crystal materials used in modern LCD displays, LCD TVs, and so forth, are typically a mixture of a plurality of different individual liquid crystal components. Ion concentration, twist elastic constant ($K_{22}$), and rotational viscosity ($\gamma_1$) are three very important parameters for the study of LC materials/mixtures and for LCD manufacture. Although there are many publications and patents regarding techniques for LC material property measurement, they are either too simplified to provide reliable and repeatable results, not sensitive enough for advanced LC materials and LCD processes to allow for the reliable and accurate detection of ultra-low ion concentrations, or overly complex.

What is needed, therefore, is a design that is better able to meet such challenges.

SUMMARY

Disclosed herein is a method for measuring the twist elastic constant ($K_{22}$) of a liquid crystal mixture under test. The method includes providing a liquid crystal test cell having a pair of electrodes; placing the liquid crystal mixture under test into the liquid crystal test cell; applying an electrical driving signal to the electrodes of the liquid crystal test cell; measuring an electrical response signal from the electrodes; and based on the electrical driving signal and the electrical response signal, and in the absence of measuring light transmitted through or reflected off of the liquid crystal test cell, determining the twist elastic constant ($K_{22}$) for the liquid crystal mixture under test.

The determining may include determining dielectric properties of the liquid crystal test cell. The determining may include determining a constant related to a geometry of the liquid crystal test cell. The determining may include using the following equation: $K_{22}=(V_{th})^2 (a\pi)^{-2} (\varepsilon_0 |\Delta\varepsilon|)$, where $V_{th}$ is the threshold minimum voltage that causes liquid crystal molecules to turn, a is a feature factor that is a function of the test cell geometry, $\varepsilon_0$ is the vacuum permittivity, and $|\Delta\varepsilon|$ is the dielectric anisotropy.

Also disclosed is a method for measuring the twist elastic constant ($K_{22}$) of a liquid crystal mixture under test. The method includes providing a liquid crystal test cell having a pair of electrodes; providing a light source that directs light into one side of the test cell and a light sensor to measure light that exits the test cell; placing the liquid crystal mixture under test into the liquid crystal test cell; applying an electrical driving signal to the electrodes of the liquid crystal test cell; measuring an amount of light that exits the test cell; and based on the electrical driving signal and the measured light, determining the twist elastic constant ($K_{22}$) for the liquid crystal mixture under test.

The amount of light that exits the test cell may be measured after the electrical driving signal has been turned off. The amount of light may have a leading edge in response to the electrical driving signal being turned on and a falling edge in response to the electrical driving signal being turned off, and the falling edge is utilized the determine the twist elastic constant. A plurality of test cells having different cell gaps may be used. A single test cell having a varying cell gap may be used. The single test cell may be formed as a wedge test cell so that the cell gap increases across a width extent of the test cell.

Also disclosed is a method for characterizing the presence of ions in an object under test. The method includes providing an object having a pair of electrodes attached thereto; applying an electrical driving signal at a given frequency to the electrodes of the object; measuring an electrical response signal from the electrodes; and based on the electrical driving signal and the electrical response signal, and in the absence of measuring light transmitted through or reflected off of the object, determining an ion distribution spectrum that includes a display of the number of ions present in the object versus the given frequency of the electrical driving signal.

The given frequency of the electrical driving signal may be varied to include a plurality of frequencies so that the number of ions present can be displayed versus the plurality of frequencies. The given frequency of the electrical driving signal may be swept from a first frequency to a second frequency. The differences between the electrical response signal at a first frequency and at a second, higher frequency may be related to the ion concentration. The measuring of the electrical response signal may include determining the resistance and capacitance of the object. The object may be a test cell containing a liquid crystal mixture to be tested. The object may be a solid object. The solid object may be a sheet of glass. The measuring of the electrical response signal may include measuring the total charge at the electrodes.

Also disclosed is a method for measuring the rotational viscosity of a liquid crystal mixture under test. The method includes providing a liquid crystal test cell having a pair of electrodes; placing the liquid crystal mixture under test into the liquid crystal test cell; applying an electrical driving signal to the electrodes of the liquid crystal test cell; measuring an electrical response signal from the electrodes; and based on the electrical driving signal and the electrical response signal, and in the absence of measuring light transmitted through or reflected off of the liquid crystal test cell, determining the rotational viscosity for the liquid crystal mixture under test.

The electrical response signal may be measured on a trailing edge of the electrical driving signal. The electrical response signal measured may be the capacitance between the pair of electrodes. A backflow effect may be ignored in determining the rotational viscosity.

Also disclosed is a method for measuring a performance parameter of a liquid crystal mixture under test. The method includes providing a liquid crystal test cell having a pair of electrodes; placing the liquid crystal mixture under test into the liquid crystal test cell; applying an electrical driving signal to the electrodes of the liquid crystal test cell; measuring an electrical response signal from the electrodes; and based on the electrical driving signal and the electrical response signal, and in the absence of measuring light transmitted through or reflected off of the liquid crystal test cell, determining the performance parameter for the liquid crystal mixture under test.

The performance parameter may be a twist elastic constant ($K_{22}$) for the liquid crystal mixture under test. The performance parameter may be an ion distribution spectrum that includes a display of the number of ions present in the liquid crystal mixture under test versus the given frequency of the electrical driving signal. The performance parameter may be a rotational viscosity for the liquid crystal mixture under test.

BRIEF DESCRIPTION OF THE DRAWINGS

The disclosure herein is described with reference to the following drawings, wherein like reference numbers denote substantially similar elements:

FIG. 6 is a flowchart of a technique for calculating $K_{22}$.

DETAILED DESCRIPTION

Figure 1:
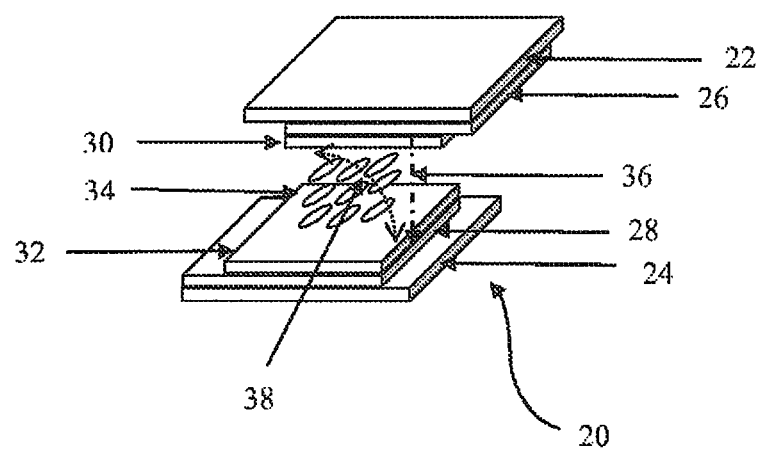
FIG. 1 is a simplified illustration of a liquid crystal test cell.

While the embodiments disclosed herein are susceptible to various modifications and alternative forms, specific embodiments thereof have been shown by way of example in the drawings and are herein described in detail. It should be understood, however, that it is not intended to limit the invention to the particular form disclosed, but rather, the invention is to cover all modifications, equivalents, and alternatives of embodiments of the invention as defined by the claims. The disclosure is described with reference to the drawings, wherein like reference numbers denote substantially similar elements.

Disclosed herein are techniques and systems related to improved techniques for measuring various parameters of liquid crystal mixtures: twist elastic constant ($K_{22}$), ion distribution spectrum, and rotational viscosity ($\gamma_1$). These techniques can be performed on any of various types of liquid crystal devices, from a simple test cell to a commercial LCD display or TV. For ease of illustration and discussion, the techniques will be shown and discussed with regard to a test cell.

In many cases, the test cell will have a single large pixel, rather than an array of pixels, but this is not necessary. Further, in some cases the test cell will have a geometry for in-plane switching (IPS), and in other cases the test cell will include a pair of parallel electrodes (known as vertically aligned, twisted nematic, and so forth).

A configuration for a parallel plate electrode test cell 20 is shown in FIG. 1. The test cell 20 includes a pair of glass substrates 22 and 24. Attached to respective ones of the glass substrates 22 and 24 are a pair of ITO electrodes 26 and 28. An alignment layer 30 and 32 is provided on respective ones of the electrodes 26 and 28. As will be discussed later in greater detail, each alignment layer may have a "rubbing direction" to control the orientation of liquid crystal molecules in contact with the alignment layer. Further, the rubbing directions on the two alignment layers may be different from each other. The space between the respective alignment layers 30 and 32 is filled with a liquid crystal mixture 34. As mentioned, the molecules in the liquid crystal mixture 34 tend to align with the nearby alignment layer. However, when an electric field 36 is created by the pair of electrodes 26 and 28, the liquid crystal molecules become oriented relative to the electric field in a manner which will be discussed in further detail below. Broken line (with arrowheads) 38 shows the range of angles through which the liquid crystal molecules might be rotatable. For example, this might vary from the longitudinal axis of the elongated LC molecule being generally parallel to the alignment layers to the longitudinal axis of the elongated LC molecule being generally perpendicular to the alignment layers.

Figure 2:
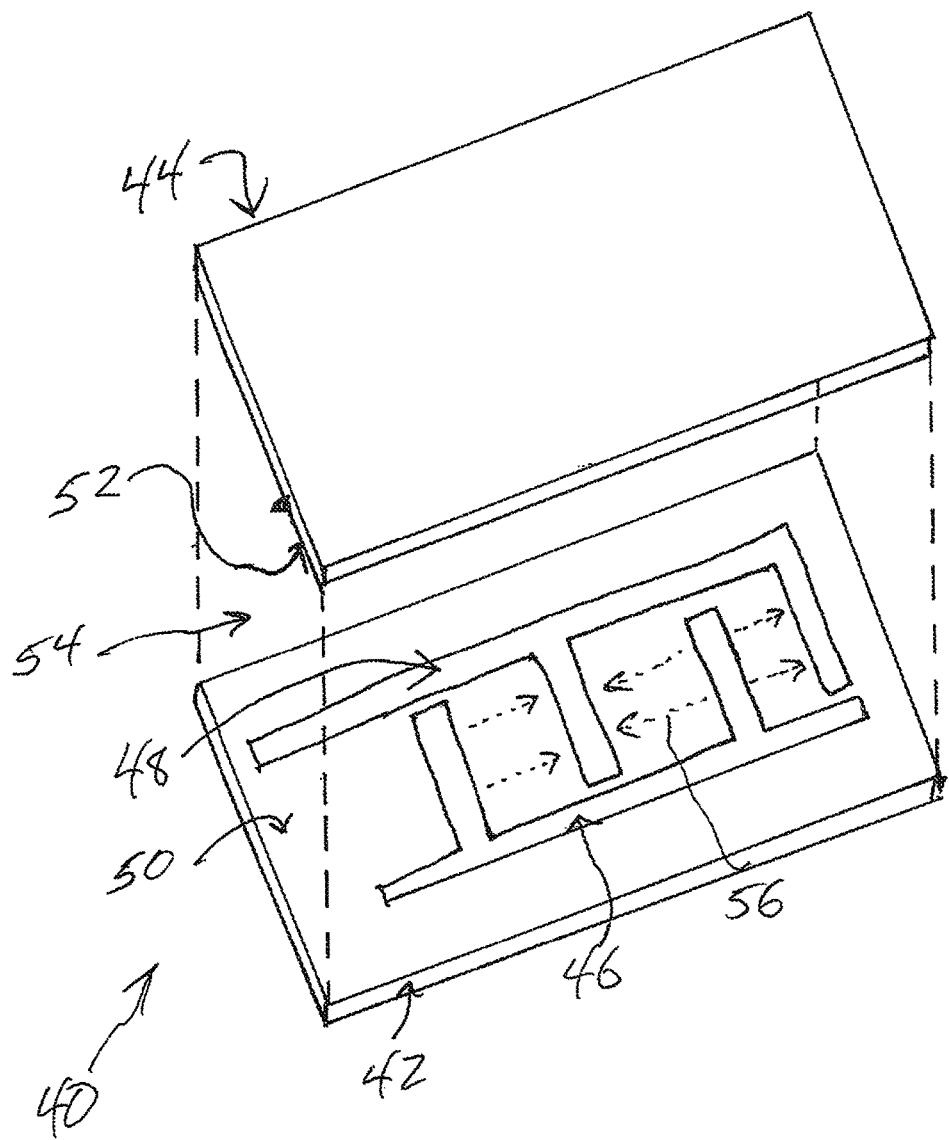
FIG. 2 is a simplified illustration of a second liquid crystal test cell, this one being configured with electrodes for in plane switching (IPS).

A configuration for an IPS electrode test cell 40 is shown in FIG. 2. The test cell 40 includes a pair of glass substrates 42 and 44. Attached on only one glass substrate 42 are a pair of ITO electrodes 46 and 48. As can be seen, in this simplified illustration of a test cell, each electrode 46 and 48 is shaped with an elongated rail from which a number of fingers (in this case, two fingers) extend transversely. Each finger extends toward the rail of the opposite electrode, so that the fingers of the respective electrodes are interleaved with each other. An alignment layer 50 is provided on top of the electrodes 46 and 48 and glass substrate 42. A second alignment layer 52 is provided on the glass substrate 44. Each alignment layer may have a rubbing direction to control the orientation of liquid crystal molecules in contact with the alignment layers 50 and 52. The space between the respective alignment layers 50 and 52 is filled with a liquid crystal mixture 54. As mentioned, the molecules in the liquid crystal mixture 54 tend to align with the nearby alignment layer. However, when an electric field 56 is created by the pair of electrodes 46 and 48, the liquid crystal molecules become oriented relative to the electric field in a manner which will be discussed in further detail below.

Figure 3:
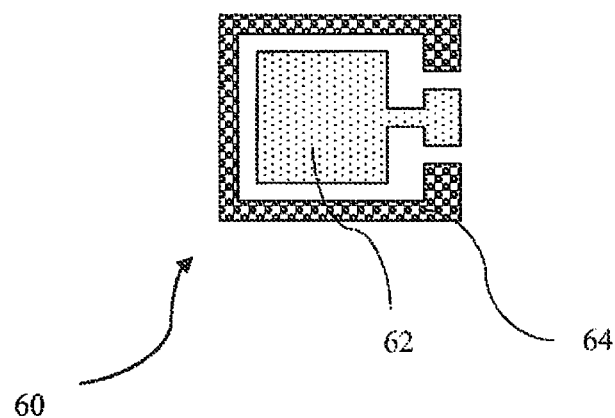
FIG. 3 is a simplified illustration of a guarded electrode configuration.

FIG. 3 shows an alternative electrode structure 60 for a test cell driven by a vertical electrical field. The structure 60 includes a centrally located driving electrode 62 which is nearly surrounded by a perimeter or guarding electrode 64. The guarding ring structure 60 reduces parasitic capacitance to a minimum in order to increase the measurement accuracy.

Figure 4:
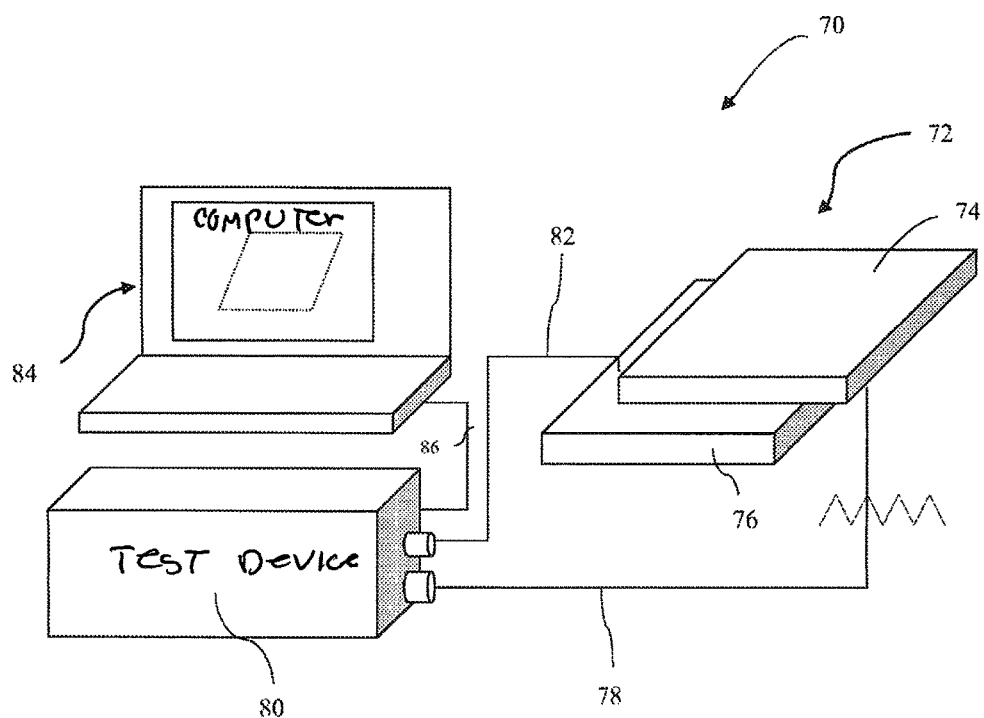
FIG. 4 is a simplified illustration of a test set-up for testing a liquid crystal mixture.

FIG. 4 shows a system 70 or arrangement for determining characteristics/parameters about liquid crystal materials. As can be seen, the system 70 includes a test cell 72 that includes at least a top electrode 74 and a bottom electrode 76. Although not shown in this drawing, a liquid crystal mixture under test has been added to the test cell 72. The test cell 72 is driven with a driving waveform 78 that is produced by a test device 80. The test device 80 receives a response signal or current 82 from the test cell 72 in response to the driving waveform 78. The system 70 may also include a PC computer 84 that may be connected to the test device 80 by a cable, such as a USB cable 86.

Figure 5:
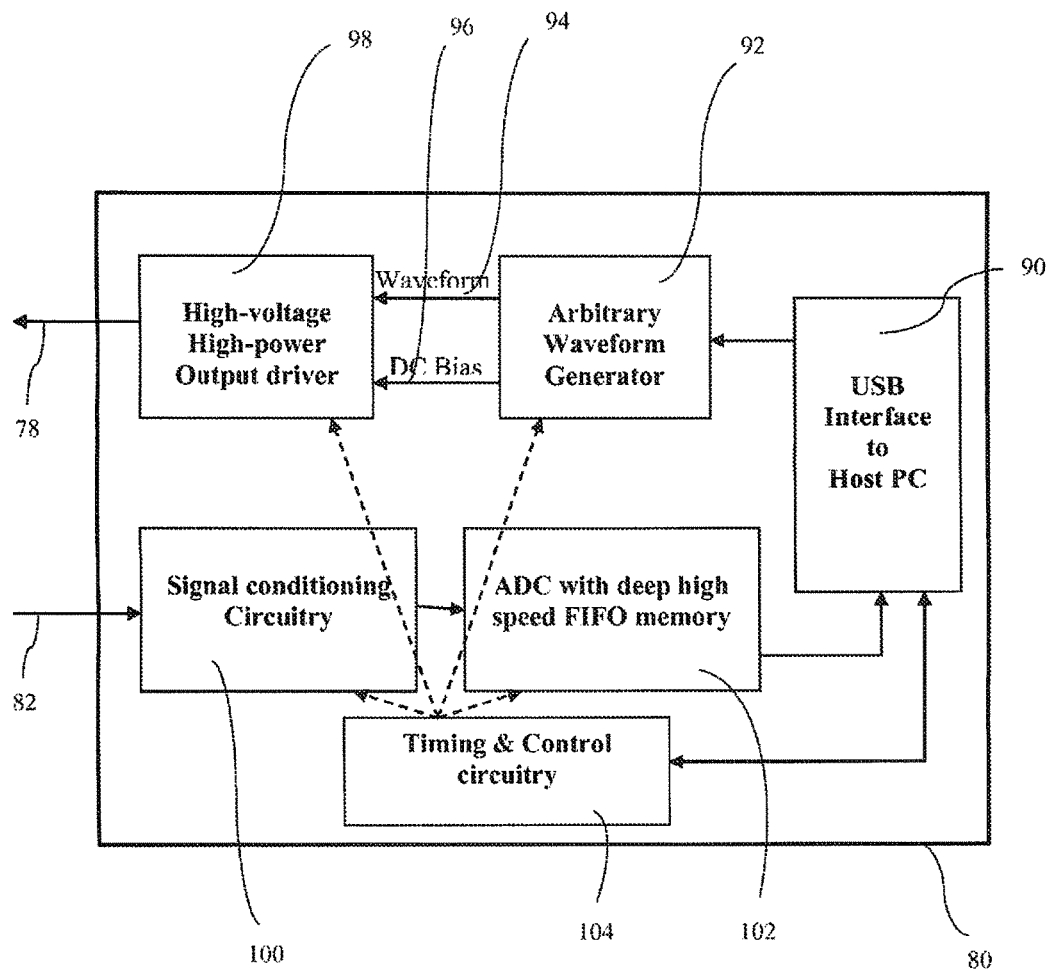
FIG. 5 is a block diagram of a test device used in the test set-up of FIG. 4.

FIG. 5 provides more details about the test device 80. In this simplified block diagram, the test device 80 includes an interface device 90 that provides a USB interface to a host PC, such as PC 84 via a USB cable 86. The interface device 90 may decode operational commands from the PC 84. Via the interface device 90, the PC 84 may provide inputs and other commands to an Arbitrary Waveform Generator (AWG) 92 (such as details about the driving waveform signal and the DC bias). The Arbitrary Waveform Generator 92 may store an arbitrary waveform and bias DC to its internal memory and provide a waveform signal 94 and a DC bias signal 96 to a High-Voltage, High-Power Output Driver 98 according to trigger signals from the Timing and Control Circuitry 104. The Driver 98 generates the driving waveform 78 that is provided to the test cell, which may provide a high driving voltage (e.g., up to +/−100V and >50 mA current driving capability). The response current 82 is provided as an input to Signal Conditioning Circuitry 100, which may amplify, convert, and filter the raw input signal to a clean voltage signal. Signal Conditioning Circuitry 100 may provide a signal to an ADC (analog-to-digital converter) with Deep High-Speed FIFO Memory 102. The ADC with Deep High-Speed FIFO Memory 102 may be triggered by the Timing and Control Circuitry 104 to convert a real-time analog signal to a digital version and record the signals into internal FIFO memory, and then to transfer the recorded data to the PC 84 for further digital processing. For example, the interface device 90 may upload measured real time data to the PC 84. The test device 80 also includes Timing and Control Circuitry 104 which communicates with each of the other components in the test device 80. The Timing and Control Circuitry 104 may generate trigger and timing signals for all functional components within the device 80, based on the operation decoded by USB interface. As can be understood, various other components may be included in the test device 80 as well, such as a power supply, and so forth.

Measurement of Twist Elastic Constant ($K_{22}$)

$K_{22}$ Measuring from C-V Curve

It should first be understood that the $K_{22}$ parameter is a constant for a given LC mixture, while other parameters are constants for a given LCD device or test cell. So the objective here is to characterize the constants other than $K_{22}$ for the test cell, and then with the LC mixture to be tested placed into the test cell, determine the $V_{th}$ (the threshold voltage, or the minimum voltage applied across the pixel that will produce even the slightest response from the pixel), and from that solve for $K_{22}$.

The relevant equation used to determine $K_{22}$ is:

$$V_{th} = \alpha \pi \frac{w}{d} \sqrt{\frac{K_{22}}{\varepsilon_0 |\Delta \varepsilon|}}, \quad \text{(Eq. 1-1)}$$

where w is the gap between electrodes, d is the cell gap, $\varepsilon_0$ is the vacuum permittivity, $|\Delta \varepsilon|$ is the dielectric anisotropy defined as $\Delta \varepsilon = \varepsilon_D - \varepsilon_\perp$, where $\varepsilon_D$ and $\varepsilon_\perp$ are dielectric constants measured when molecules are aligned in parallel or aligned vertically to the applied electric field, and $\alpha$ is a new term introduced here—a test cell feature factor for $K_{22}$ calculation. In the normal case, $\alpha \neq 1$. Therefore, we introduce equation:

$$\alpha = ad + b \quad \text{(Eq. 1-2)}$$

which takes cell gap, d, into account. Our observations have found that $b \cong 1$ for most test cell structures (particularly when the test cells have a large pitch (related to the distance between electrodes), but a varies greatly for different test cell structures as it is a function of the structure.

$$\text{Let } B = \pi w \sqrt{\frac{K_{22}}{\varepsilon_0 |\Delta \varepsilon|}} \quad \text{(Eq. 1-3)}$$

and then Eq. 1-1 can then be represented as:

$$K_{22} = \varepsilon_0 |\Delta \varepsilon| \left(\frac{B}{\pi w}\right)^2 \text{ and} \quad \text{(Eq. 1-4)}$$

$$V_{th} = (a + 1/d) * B \quad \text{(Eq. 1-5)}$$

So, d and w are known for the IPS test cell, and a can be measured for the IPS test cell, by test previously performed for three different gap test cells. For example, a first test cell with a gap of d1 a second test cell with a gap of d2, and a third test cell with a gap of d3 could be used and a can be determined therefrom. Then, for each test cell used in the system 70, one can obtain a curve of Capacitance versus Voltage (C-V curve). From each of these curves, the $V_{th}(d)$ can be determined. Then, one can linear fit $V_{th}(d)$ as function of (1/d), to get "a" and "B". From equation 1-3, one gets $K_{22}$. Moreover, theoretically, a single wedged cell could be used instead of three or more cells with different spacing.

In addition, it may be desirable to use an electrical driving signal with a small magnitude (e.g., in the range of 0.1 volts) so that the molecules do not move very much.

A flowchart 120 for this technique is show in FIG. 6. First, a set of IPS test cells are selected. The rubbing direction may be in the range of 0 to 3 degrees for a positive LC mixture and in the range of 87 to 90 degrees for a negative LC mixture. Next, the test cell is filled with the LC mixture to be tested. The $V_{th}$ is then measured for all three test cells (each have a different cell gap). The cell feature factor is then derived by fitting (Equation 15) all the above values for $V_{th}$ using their corresponding cell gap as the variable.

As can be appreciated, this technique introduces IPS cell feature factor, α, for accurate calculation of K22 with any cell gap. Cell feature factor can also be extracted from a single wedge cell using the same principle. Without using the α factor, the measurements used by others may only be reasonably accurate at d=0 or w=∞. Lastly, this method applies to both positive and negative liquid crystal mixture types.

$K_{22}$ Measuring from T-t Data

An alternative to the above approach determines K22 from driving the test cell and measuring the optical transmittance of the test cell. The base equations used are $$\gamma_1 \frac{\partial \phi(z,t)}{\partial t} = K_{22} \frac{\partial^2 \phi(z,t)}{\partial z^2} \quad \text{(Eq. 2-1)}$$

$$\phi = \phi_0 + \delta \quad \text{(Eq. 2-2)}$$

When $\delta \to 0$, Eq. 2-1 can be simplified to:

$$\delta(z,t) = \delta_0 e^{\frac{-K_{22}}{\gamma_1 d^2}} \sin\left(\frac{\pi z}{d}\right) \quad \text{(Eq. 2-3)}$$

and translated to transmittance equation $$T(t) = T_0 e^{\beta^2 \frac{-K_{22}}{\gamma_1 d^2} t} \quad \text{(Eq. 2-4)}$$

Eq. 2-4 can be further simplified when test cell is designed as w=1 mm, d=8 um, and new parameter β is introduced (β

≅1 or ln (3) ≅1.09). In particular, β ≅1 when the electrode gap is much larger than the cell gap $$\left(\frac{w}{d} \to \infty\right).$$

With this technique, a single test cell or wedged cell (cell gap d continuously changed) can be used. This includes measuring $K_{22}$ using optical decay method. By fitting equation 2-4 into the measured T(t), one gets τ. Once the rotational viscosity $\gamma_1$ and cell gap d is obtained from other measurements, K22 is then obtained from $$\tau \equiv \frac{2\gamma_1 d^2}{K_{22}}.$$

[Again we use fitting here to determine $K_{22}$. With β=1 or 1.09, for given γ1 and d (determined by test cell and liquid crystal mixture), the T-t curve is a set of T(t) and t data pairs, from which we can curve fit with equation 2-4 and find out $K_{22}$.]

Figure 9:
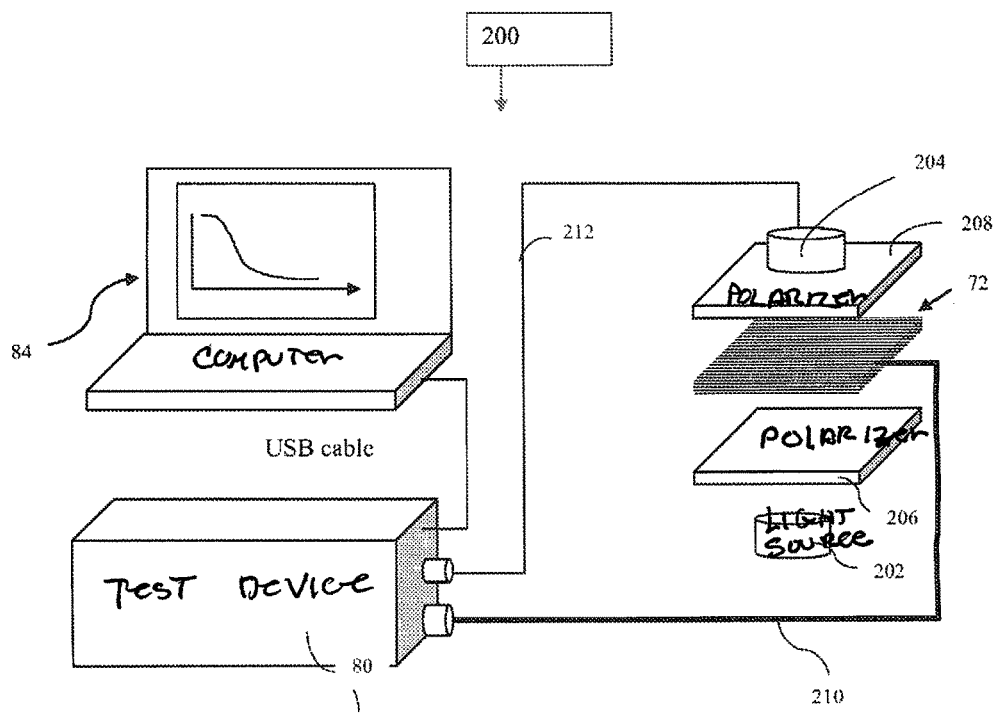
FIG. 9 is a simplified illustration of a second test set-up for testing a liquid crystal mixture.

FIG. 9 shows a system 200 or arrangement for determining characteristics/parameters about liquid crystal materials. As can be seen, the system 200 includes the test cell 72. Although not shown in this drawing, a liquid crystal mixture under test has been added to the test cell 72. The test cell 72 is driven with a driving waveform 210 that is produced by a test device 80. The system 200 also includes a light source 202, a light sensor (or photodetector) 204, and a pair of polarizers 206 and 208. The test device 80 receives a response signal 212 from the light sensor 204 in response to the driving waveform 78. The system 200 may also include a PC computer 84 that may be connected to the test device 200 by a cable, such as a USB cable 86.

Figure 7:
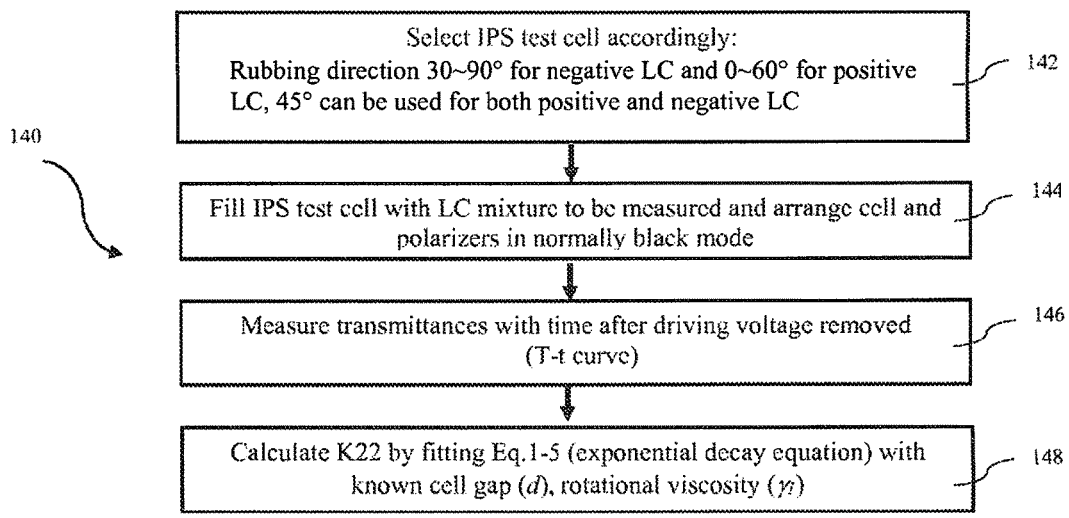
FIG. 7 is a flowchart of a second technique for calculating $K_{22}$.

A flowchart 140 for this technique is show in FIG. 7. First, an IPS test cell is selected (142). The rubbing direction may be in the range of 40 to 90 degrees for a negative NLC mixture and in the range of 0 to 50 degrees for a positive NLC mixture. Note, that 45 degrees could be used for both positive and negative NLCs, for example. Next, the test cell is filled (144) with the LC mixture to be tested. The light source is turned on and the polarizers are arranged into a normally black mode. The transmittances are then measured (146) on the trailing edge of the drive voltage. In other words, the drive voltage is returned to zero and the LC test cell should return from a light transmitting state to a light blocking (black) state. It is this falling edge that is analyzed. The $K_{22}$ constant is then calculated (148) for the LC mixture under test by fitting Equation 2-4 above (the exponential decay equation) with measured transmittance, cell gap, and rotational viscosity (γ1). The general idea is to fit $$T(t) = T_0 e^{\frac{-t}{\tau}}$$

to get decay time constant, τ., then $$\tau \equiv \frac{2\gamma_1 d^2}{K_{22}}$$

use to calculate $K_{22}$. We assume rotational viscosity (γ1) and cell gap (d) are known parameters or can be measured with our ALCT.

Ion Distribution Spectrum Characterization

As stated previously, liquid crystal materials used in modern LCD displays, LCD TVs, and so forth, are typically a mixture of a plurality of different individual liquid crystal components. While individual LC components do not typically include ions therein, it is quite common for LC mixtures to contain ions, either due to the mixing of different components or due to contaminants finding their way into the mixture. Further, these ions can cause performance issues with the LCDs, such as image sticking. For this reason, it is desirable to know more about the ions in mixtures. Up until now, this has only included measuring the concentration of ions in LC mixtures.

Disclosed herein are techniques for looking at ion density (charge/charge density) also in this writing as a function of frequency of the driving signal for a LC mixture under test. By looking at this "ion distribution spectrum," one can often recognize exactly what type of ion is present in the mixture. Much like with fingerprints, the ion distribution spectrum of an LC mixture provides a ready ability to distinguish between different types of ions that may be present in the mixture. As will be discussed, a driving waveform that sweeps through a range of waveform frequencies (for example, the waveform may be triangular with the frequency being varied). As but one example, the frequency range for the sweep may be from 0.0001 Hz to 1 kHz. As the frequency is swept, the total number of ions measurable up to each scan frequency is measured. The measurement includes determining the total charge and subtracting the charge due to the dielectric constant. This generates a plot of ions versus frequency which provides the user information about which ions or which types of ions may be present. Relative low frequencies such as this are employed in part because the resistance and capacitance do not vary significantly at such frequencies.

The current (I) measured at the output of the LCD device, corresponding to the applied or driving voltage (V), is defined by:

$$I = \frac{dQ}{dt} = \frac{d(CV)}{dt} + \frac{V}{R} + qAd\frac{dn}{dt}, \quad \text{(Eq. 3-1)}$$

where n is ion density of liquid crystal mixture, C is capacitance of test cell filled with liquid crystal mixture to be measured, and R is parasitic resistance of test cell, and connecting wires, q is the charge of electron, A this the cell area, and d is the cell gap. With a DC balanced driving waveform, we integrate both sides of Eq. 3-1. Since V is time-varying and not symmetrical and R can also be assumed as a constant, the integral of V/R term is zero, and get:

$$nqAd = \int_{-\frac{T}{2}}^{\frac{T}{2}} Idt - 2CV_0 \quad \text{(Eq. 3-2)}$$

where T is the period of the driving waveform.

For modern NLC mixtures used in LCD commercial products, C is almost a constant at frequencies lower than 1 KHz for the same applied $V_0$. Then the total ion density at frequency $$f_i = \frac{1}{T_i}$$

can be represented as:

$$n(T_i) = \frac{1}{qAd} \int_{-\frac{T_i}{2}}^{\frac{T_i}{2}} I dt - 2CV_0 \quad \text{(Eq. 3-3)}$$

Normally, the ion response time is much slower than 1 mS. So, $n(f_i \geq 1000\ Hz)=0$, or a small number (bias).

Eq. 3-3 can be used to characterize the ion frequency responses (referred as ion spectrum thereafter) by Eq. 3-4 as:

$$\Delta n_i(T_i) = n(T_i - \Delta t) - n(T_i + \Delta t) \quad \text{(Eq. 3-4)}.$$

Equation 3-4 represents an ion increment with frequency difference of $\Delta f = 1/(2*\Delta t)$, which is the "color" or "finger prints" of a particular ion. The same principle has been used in gas/liquid chromatography instruments and mass/optical spectrometers for material study and analysis.

The test device 80 (ALCT from Instec, Inc.) is particularly designed for this ion spectrum measuring with the lowest frequency down to 0.0001 Hz.

Figure 10:
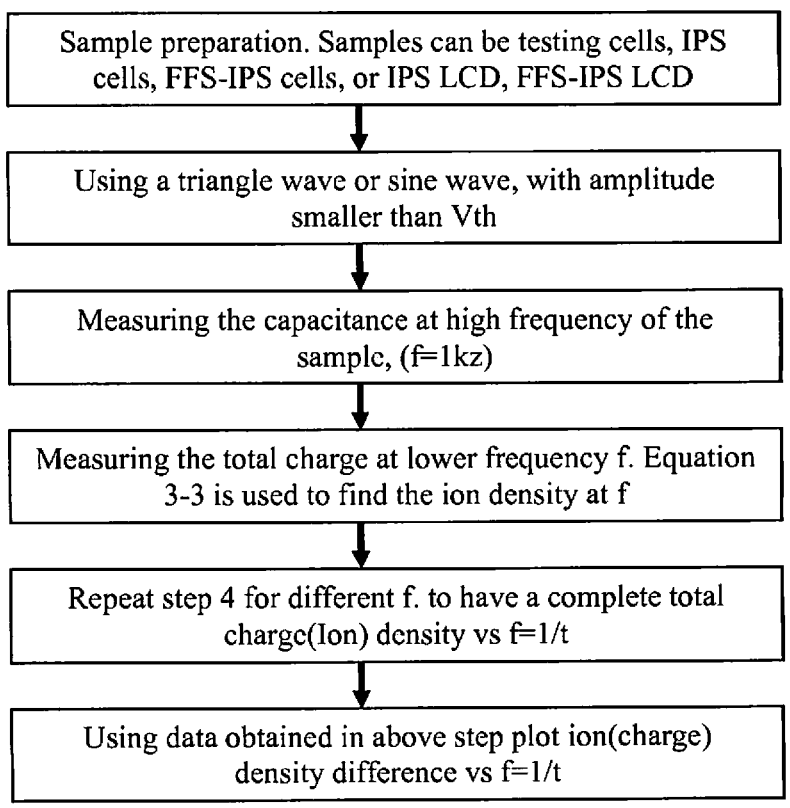
FIG. 10 is a flowchart of a technique for calculating ion density.

Please see the flowchart of FIG. 10.

As can be appreciated, this is the first spectral analysis method developed for liquid crystal mixture ion characterization. This method can be applied to test cells and real TFT and other LCD panels. Further, this method is applicable to all kinds of LC device structures including IPS, FFS-IPS, VA types, and others. This method can be used to identify one or more particular components in a liquid crystal mixture that has a significant contribution to one or more of typical LCD defects such as flicker and image sticking. This method can also be applied to measure ion movement or charged molecule displacement for solid materials, such as glass substrates of LCD, OLED, or others. This method can also be used for measuring ion concentration of liquid or powdered, film or bulk electrodes, such as polyimide, bi-fingered electrodes.

Summarized differently, the measurement procedures include the following:

(1) Samples to be measured could be test cells (parallel capacitance type or IPS, FFS-IPS type), or real TFT panels (VA, TN, IPS or FFS-IPS, and so on). For real panel measurement, the gate voltage needs to be applied following the TFT design.

(2) Measure the R and C of the sample at high frequency, then do the same at low frequency. The difference between the two reflects the ion concentration, more ions, the difference is bigger.

Ion impurity measurement principles:

$$I = \frac{dQ}{dt} = \frac{d(CV)}{dt} + \frac{V}{R} + \frac{dn}{dt},$$

where n is the ion charge. At steady state, for nematic LC material, C is the same for $\pm V_0$, and C is constant at frequency lower than 1 Khz.

$n = \int I dt - 2CV_0$ at high frequency such as 1 Khz, n=0, since ions to slow to follow the 1 Khz.

Therefor the ions at lower frequency is n(f)=Q(f)−Q(1 Khz)

Where f is the frequency of the applied triangle wave or sine wave.

Normally, n is goes bigger as f goes to smaller, n also goes bigger as Temperature goes up. Same principles can also applied to IPS or FFS-IPS structure. Same principles applies to $V_0$ bigger or smaller than $V_{th}$. Results are compared with conventional triangle method which require the observation of ion current bump. Advantage for this new method is that there is no need to find the bump in the current curve.

For the first time, the ion spectrum method is introduced for instrumentation, is extended to a real TFT panel, and is applied to IPS and FFS-IPS structure LC cells or TFT panels. This method can also be applied to measure ion movement or charged molecule displacement for solid materials, such as glass substrates of LCD, OLED. This method can also be used for measuring ion concentration of other materials, which are not liquid crystals, such as isotropic liquid or powered, film or bulk, such as polyimiade, bi-fingered electrodes. This is all accomplished by comparing R and C at low frequency driving signal to R and C at high frequency driving signal.

Measuring Rotational Viscosity, γ1 (or gamma1)

First of all, it should be understood that from the current, one can derive the capacitance, and from capacitance one can derive the angle of the LC molecule. The shear flow equation is:

$$a(\theta)\frac{\partial V_x(z,t)}{\partial z} + b(\theta)\frac{\partial \theta(z,t)}{\partial t} = \sigma(t) \quad \text{(Eq. 4-1)}$$

The rotational equation, where θ is the angle between the director and the z axis (i.e., the angle of the LC molecule), is:

$$\gamma_1 \frac{\partial \theta(z,t)}{\partial t} = -b(\theta)\frac{\partial V_x(z,t)}{\partial z} + g(\theta)\frac{\partial^2 \theta(z,t)}{\partial z^2} + \frac{1}{2}\frac{dg(\theta)}{d\theta}\left[\frac{\partial \theta(z,t)}{\partial z}\right]^2 - \frac{1}{2}\varepsilon_0 \Delta\varepsilon E^2(z,t)\sin 2\theta(z,t) \quad \text{(Eq. 4-2)}$$

Where $$a(\theta) = \alpha_1 \sin^2\theta(z,t)\cos^2\theta(z,t) + \frac{1}{2}[-\gamma_2\cos 2\theta(z,t) + \alpha_3 + \alpha_4 + \alpha_5] \quad \text{(Eq. 4-3)}$$

$$b(\theta) = \frac{1}{2}[\gamma_2\cos 2\theta(z,t) - \gamma_1] \quad \text{(Eq. 4-4)}$$

Where $$\alpha_{45} = \alpha_4 + \alpha_5 \quad \text{(Eq. 4-5)}$$

$$\gamma_1 = \alpha_3 - \alpha_2 \approx -\alpha_2,\ \gamma_2 = \alpha_3 + \alpha_2 \approx -\gamma_1 \quad \text{(Eq. 4-6)}$$

$$\alpha_3 \approx 0$$

$$g(\theta) = K_{11}\sin^2\theta + K_{33}\cos^2\theta, \quad \text{(Eq. 4-7)}$$

When backflow is ignored (which we believe has not previously been done), the equation reduces to:

$$\gamma_{10}\frac{\partial \theta(z,t)}{\partial t} = g(\theta)\frac{\partial^2 \theta(z,t)}{\partial z^2} + \frac{1}{2}\frac{dg(\theta)}{d\theta}\left[\frac{\partial \theta(z,t)}{\partial z}\right]^2 - \frac{1}{2}\varepsilon_0\Delta\varepsilon E^2(z,t)\sin 2\theta(z,t) \quad \text{(Eq. 4-7)}$$

Boundary condition due to the anti-parallel rubbing:

$$\theta(0,t)=\theta(d,t)=\theta_0 \quad \text{(Eq. 4-8)}$$

$$V_x(d,t)=-V_x(0,t) \quad \text{(Eq. 4-9)}$$

Furthermore, we take:

$$\theta(z, t) = \theta(d - z, t) \quad \text{(Eq. 4-10)}$$

$$\left.\frac{\partial \theta(z, t)}{\partial z}\right|_{z=\frac{d}{2}} = 0 \quad \text{(Eq. 4-11)}$$

Also, $$V_x\left(\frac{d}{2}\right) = 0 \quad \text{(Eq. 4-12)}$$

$$\sigma(t) = kV_x(0, t) \quad\text{----}> V_x(0, t) = \frac{\sigma(t)}{k} \quad \text{(Eq. 4-13)}$$

$$V_x(0, t) = \frac{\beta}{a(\theta_0)}\sigma(t) \quad \text{(Eq. 4-14)}$$

$$k = \frac{a(\theta_0)}{\beta} \quad \text{(Eq. 4-15)}$$

where $\beta$ is slip length,
k is the friction coefficient at the liquid and solid interface
n=(sin θ, 0, cos θ) is the director
P=E(Δε sin θ cos θ, 0, $\varepsilon_\perp$ sin$^2$ θ+$\varepsilon_\parallel$cos$^2$ θ) is the induced polarization
$\varepsilon_{eff}=\varepsilon_\perp$ sin$^2$ θ+$\varepsilon_\parallel$ cos$^2$ θ is the effective dielectric constant $$C_t(z, t) = \frac{\varepsilon_{eff}\varepsilon_0 A}{dz}, \frac{1}{C_t(t)} = \frac{1}{\varepsilon_0 A}\int\frac{dz}{\varepsilon_{eff}} \quad \text{(Eq. 4-16)}$$

The θ(z, t) can be calculated from Equations 4-1 and 4-2, if backflow is included. Or equation 4-7 if backflow is ignored assuming all alpha's, $\alpha_i$ are known. $C_t(t)$ then is calculated from equation 4-16. The calculation is done by fitting theoretical $C_t(t)$ with measured $C_m(t)$. From the fitting, we can extract alpha's, α, and $\gamma_1$.

Figure 8:
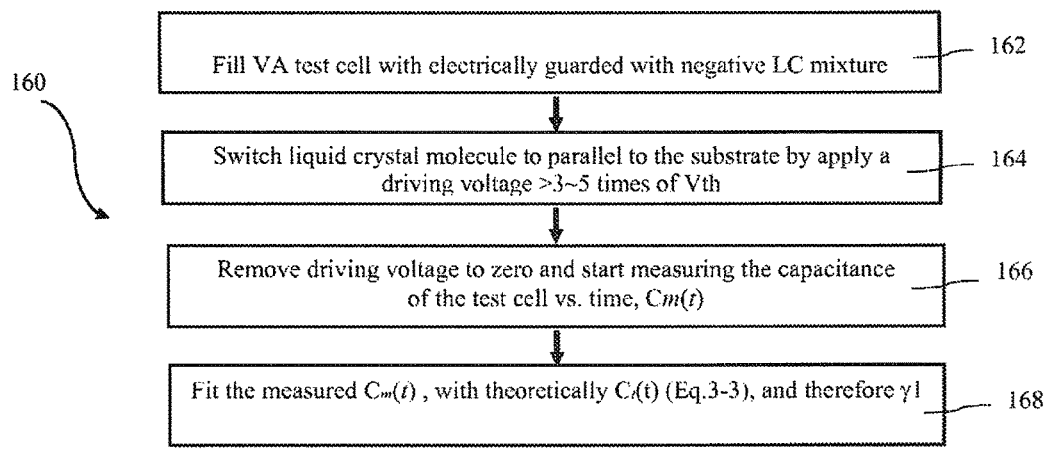
FIG. 8 is a flowchart of a technique for calculating rotational viscosity.

FIG. 8 includes a flowchart 164 calculating rotational viscosity. First, the test cell (e.g., the test cell 20 of FIG. 1) is filled (162) with a negative liquid crystal mixture. The test cell may include one or more electrically guarded electrodes 60 as shown in FIG. 3. Next, the liquid crystal modules are switched (164) to being parallel to the substrate by applying a driving voltage that is more than 3 to 5 times greater than the threshold voltage. Then, the driving voltage is removed and falls to zero, so that the capacitance of the test cell versus time can be measured (166). Following this, the measured $C_m(t)$ is fit with the theoretical $C_t(t)$ to determine (168) gamma1, the rotational viscosity. Note that it is again only the trailing edge that is analyzed and not both the leading edge and the trailing edge.

While the embodiments of the invention have been illustrated and described in detail in the drawings and foregoing description, such illustration and description are to be considered as examples and not restrictive in character. For example, certain embodiments described hereinabove may be combinable with other described embodiments and/or arranged in other ways (e.g., process elements may be performed in other sequences). Accordingly, it should be understood that only example embodiments and variants thereof have been shown and described.

We claim:

1. A method for measuring the twist elastic constant ($K_{22}$) of a liquid crystal mixture under test, the method comprising:
   providing a liquid crystal test cell having a pair of electrodes;
   providing a light source that directs light into one side of the test cell and a light sensor to measure the light that exits the test cell;
   placing the liquid crystal mixture under test into the liquid crystal test cell;
   applying an electrical driving signal to the electrodes of the liquid crystal test cell;
   measuring an amount of the light that exits the test cell to form a measured light; and
   based on the electrical driving signal and the measured light, determining the twist elastic constant ($K_{22}$) for the liquid crystal mixture under test; the method further including providing a pair of polarizers on opposite sides of the liquid crystal test cell;
   wherein the pair of polarizers are arranged so that light from the light source does not exit the combination of the pair of polarizers and the liquid crystal test cell in the absence of an electrical driving signal to the electrodes of the liquid crystal test cell.

2. A method as defined in claim 1, wherein the amount of light that exits the test cell is measured after the electrical driving signal has been turned off.

3. A method as defined in claim 2, wherein the amount of the light has a leading edge in response to the electrical driving signal being turned on and a falling edge in response to the electrical driving signal being turned off, and the falling edge is utilized to determine the twist elastic constant.

4. A method as defined in claim 1, wherein a plurality of liquid crystal test cells having different cell gaps are used.

5. A method as defined in claim 1, wherein a single liquid crystal test cell having a varying cell gap is used.

6. A method as defined in claim 5, wherein the single test cell is formed as a wedge test cell so that the cell gap increases across a width extent of the test cell.

7. A method as defined in claim 1, wherein the pair of electrodes in the liquid crystal test cell are In-Plane Switching (IPS) electrodes that lie in a single plane.

8. A method as defined in claim 7, wherein the pair of electrodes include a first electrode at least nearly surrounded by a perimeter electrode.

9. A method as defined in claim 1, wherein the pair of electrodes in the liquid crystal test cell are vertically-aligned parallel electrodes that lie in parallel planes.

10. A method as defined in claim 1, wherein the measurement of the amount of light that exist the test cell is a measurement of the transmittance of the test cell.

11. A method as defined in claim 1, wherein the step of determining of the twist elastic constant uses a distance of a cell gap of the liquid crystal test cell and a rotational viscosity of the liquid crystal mixture under test.

\* \* \* \* \*